United States Patent [19]

Cunkle et al.

[11] Patent Number: 5,235,056

[45] Date of Patent: Aug. 10, 1993

[54] SUBSTITUTED 1-HYDROXY-2,6-DIARYL-4-PIPERIDONE KETALS AND POLYMER COMPOSITIONS STABILIZED THEREWITH

[75] Inventors: Glen T. Cunkle, Stamford, Conn.; Donald J. Sabrsula, Peekskill, N.Y.

[73] Assignee: Ciba-Geigy Corporation, Ardsley, N.Y.

[21] Appl. No.: 872,740

[22] Filed: Apr. 22, 1992

[51] Int. Cl.⁵ .......................... C07D 211/22
[52] U.S. Cl. ................... 546/187; 546/242; 546/207; 524/99
[58] Field of Search ............ 546/187, 242, 207; 524/99

[56] References Cited

U.S. PATENT DOCUMENTS

| | | | |
|---|---|---|---|
| 4,316,996 | 2/1982 | Collonge et al. | 568/784 |
| 4,548,639 | 10/1985 | Riebel et al. | 71/94 |
| 4,578,410 | 3/1986 | Takahashi et al. | 524/102 |
| 4,668,721 | 5/1987 | Seltzer et al. | 524/95 |
| 4,782,105 | 11/1988 | Ravichandran et al. | 524/236 |
| 4,876,300 | 10/1989 | Seltzer et al. | 524/100 |
| 4,898,901 | 2/1990 | Ravichandran et al. | 524/237 |
| 5,001,233 | 3/1991 | Murray et al. | 540/29 |

OTHER PUBLICATIONS

Tetrahedron, 1963, vol. 19, pp. 2135–2143, M. Balasubramanian, et al.

J. Org. Chem. 1988, 53, pp. 5353–5355, Eaton et al.

*Primary Examiner*—Marianne M. Cintins
*Assistant Examiner*—Michael B. Hydorn
*Attorney, Agent, or Firm*—Luther A. R. Hall

[57] ABSTRACT

1-Hydroxy-2,6-diaryl-4-piperidone ketal derivatives, such as the compound of formula I

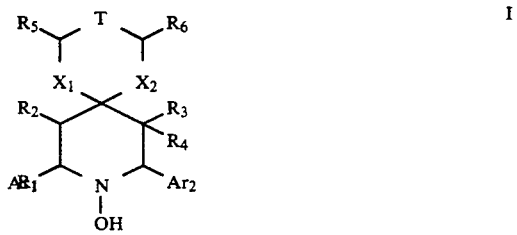

wherein $Ar_1$ and $Ar_2$ are each phenyl, $R_1$ to $R_6$ are all hydrogen, $X_1$ and $X_2$ are each —O— and T is a direct bond, are novel compounds and are effective process stabilizers, such as polypropylene, for polymers processed at elevated tempertures providing both good melt flow stabilization and good resistance against discoloration during said processing.

20 Claims, No Drawings

SUBSTITUTED 1-HYDROXY-2,6-DIARYL-4-PIPERIDONE KETALS AND POLYMER COMPOSITIONS STABILIZED THEREWITH

The instant invention pertains to novel 1-hydroxy-2,6-diaryl-4-piperidone ketal derivatives which are process stabilizers for polymers processed at elevated temperatures.

BACKGROUND OF THE INVENTION

U.S. Pat. Nos. 4,668,721; 4,782,105; 4,876,300 and 4,898,901 describe hydroxylamine compounds, which are structurally distinct from the instant compounds, as process stabilizers for polymeric compositions.

U.S. Pat. No. 4,316,996 teaches 1-hydroxy-2,6-dialkylpiperidines a effective in preventing the discoloration of phenolic antioxidants.

1-Hydroxy-2,2,6,6-tetramethyl-4-piperidone ketals and 1-hydroxy-2,2,6,6-tetramethylpiperidine derivatives are known as effective light stabilizers, but these materials are not known as being effective process stabilizers. Said compounds are structurally distinct from the instant compounds.

1-Hydroxy-2,6-diaryl-4-acyloxypiperidines are described in copending U.S. patent application Ser. No. 696,695.

The instant 1-hydroxy2,6-diaryl-4-piperidone ketal derivatives are novel and are not described or suggested in the prior art.

OBJECTS OF THE INVENTION

One object of this invention is to provide new 1-hydroxy-2,6-diaryl-4-piperidone ketal derivatives which are effective process stabilizers for polymers processed at elevated temperature.

Another object of the instant invention is to provide polymer composition stabilized against degradation during processing by the presence of an instant 1-hydroxy-2,6-diaryl-4-piperidone ketal derivative.

A further object of this invention is to provide new valuable intermediates required to prepare the 1-hydroxy-2,6-diaryl-4-piperidone derivatives.

DETAILED DISCLOSURE

The instant invention pertains to a 1-hydroxy-2,6-diaryl-4-piperidone ketal derivative of formula I, II or III

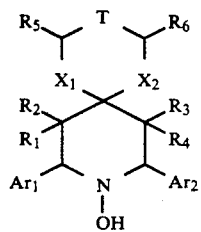

I

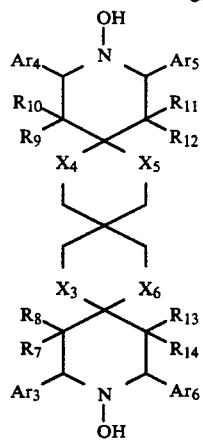

II

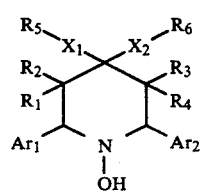

III wherein $Ar_1$, $Ar_2$, $Ar_3$, $Ar_4$, $Ar_5$ and $Ar_6$ are independently aryl of 6 to 10 carbon atoms or said aryl substituted by one to three substituents selected from the group consisting of alkyl of 1 to 20 carbon atoms, cycloalkyl of 5 to 12 carbon atoms, phenylalkyl of 7 to 15 carbon atoms, —$COOR_{15}$ where $R_{15}$ is hydrogen or alkyl of 1 to 20 carbon atoms, —$COR_{16}$ where $R_{16}$ is alkyl of 1 to 20 carbon atoms, —$NR_{17}R_{18}$ where $R_{17}$ and $R_{18}$ are independently hydrogen or alkyl of 1 to 20 carbon atoms, —$SR_{19}$ where $R_{19}$ is aryl of 6 to 10 carbon atoms or alkyl of 1 to 20 carbon atoms; —OH, —$OCH_3$, —CN, —$CF_3$, —$NO_2$, —F, —Cl, —Br and —I;

$R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently hydrogen; a linear or branched alkyl of 1 to 30 carbon atoms; said alkyl terminated with —$OR_{20}$, —$NR_{21}R_{22}$, —$SR_{23}$, —$COOR_{24}$ or —$CONR_{25}R_{26}$, where $R_{20}$, $R_{21}$, $R_{22}$, $R_{23}$, $R_{24}$, $R_{25}$ and $R_{26}$ are independently hydrogen, alkyl of 1 to 20 carbon atoms or alkenyl of 3 to 18 carbon atoms; said alkyl interrupted by one or more —O—, —S—, —SO—, —$SO_2$—, —CO—, —COO—, —OCO—, —$CONR_{27}$—, —$NR_{27}CO$— or —$NR_{28}$— where $R_{27}$ and $R_{28}$ independently have the same meaning as $R_{20}$; alkenyl of 3 to 20 carbon atoms; aryl of 6 to 10 carbon atoms; said aryl substituted by one to three substituents selected from the group consisting of alkyl of 1 to 20 carbon atoms, cycloalkyl of 5 to 12 carbon atoms, phenylalkyl of 7 to 15 carbon atoms, —$COOR_{29}$ where $R_{29}$ is hydrogen or alkyl of 1 to 20 carbon atoms, —$COR_{30}$ where $R_{30}$ is alkyl of 1 to 20 carbon atoms, —$NR_{31}R_{32}$ where $R_{31}$ and $R_{32}$ are independently hydrogen or alkyl of 1 to 20 carbon atoms, —$SR_{33}$ where $R_{33}$ is aryl of 6 to 10 carbon atoms or alkyl of 1 to 20 carbon atoms; —OH, —$OCH_3$, —CN, —$CF_3$, —$NO_2$, —F, —Cl, —Br and —I;

T is a direct bond or —CR$_{34}$R$_{35}$— where R$_{34}$ and R$_{35}$ independently have the same meaning as R$_1$; and X$_1$, X$_2$, X$_3$, X$_4$, X$_5$ and X$_6$ are independently —O—, —S— or —NR$_{36}$— where R$_{36}$ has the same meaning as R$_{20}$.

All possible geometric isomers and stereoisomers which are predictable are to be included in the scope of this invention.

Preferably, each of Ar$_1$ through Ar$_6$ is phenyl.

Preferably, R$_1$ through R$_4$ and R$_7$ through R$_{14}$ are independently hydrogen or methyl.

Preferably, for formula I, R$_5$ and R$_6$ are hydrogen and T is a direct bond; or R$_5$ is hydrogen and R$_6$ is tetradecyl, and T is a direct bond; or R$_5$ and R$_6$ are hydrogen and T is —C(CH$_3$)$_2$—.

Preferably, for formula III, R$_5$ and R$_6$ are alkyl of 6 to 12 carbon atoms.

Preferably, X$_1$ through X$_6$ are —O—.

The 1-hydroxy-2,6-diaryl-4-piperidone petals of this invention exhibit surprising properties distinct from the closest prior art compounds.

The instant compounds are structurally distinct from said prior art compounds. The functionality allows for the synthesis of high molecular weight material which has low volatility, better compatibility with a wide variety of substrates and low extractability. The instant compounds provide both melt flow stabilization and good resistance against discoloration during polymer processing at elevated temperatures. The instant compounds have superior hydrolytic stability over the state of the art phosphite stabilizers and exhibit superior long term heat aging and oxidative induction times over the state of the art hydroxylamine stabilizers.

The instant invention also pertains to stabilized compositions which comprise
(a) an organic polymer subject to thermal and oxidative degradation; and
(b) an effective stabilizing amount of a compound of formula I, II or III.

The instant invention also pertains to such stabilized compositions which also contain an effective stabilizing amount of a phenolic antioxidant.

The instant invention also pertains to precursor intermediates required for the preparation of the instant compounds of formula I, II or III by oxidation using dimethyldioxirane or another oxidation agent. These precursor intermediates have the formula IV, V or VI

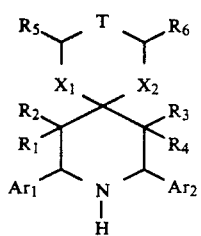

IV

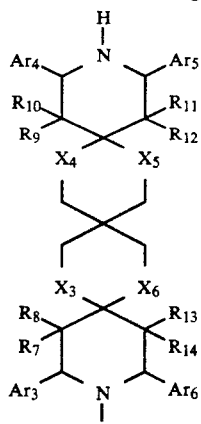

V

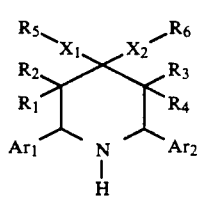

VI wherein Ar$_1$ to Ar$_6$, R$_1$ to R$_{14}$, T and X$_1$ to X$_6$ are as defined above.

The instant compounds may be prepared by general methods taught in the prior art. 2,6-Diphenyl-4-piperidone, 2,6-diphenyl-3-methyl-4-piperidone and 2,6-diphenyl-3,5-dimethyl-4-hydroxypiperidone are prepared according to the procedure of Balasubramanian, M.; Padma, N., Tetrahedron, 19, 2135 (1963). Oxidation of secondary amines to hydroxylamines using dimethyldioxirane has been reported by Murray and Singh; Synthetic Communications 19, 3509 (1989). Dimethyldioxirane solutions in acetone are prepared by the procedure of Eaton and Wicks; J. Org. Chem. 1988, 53, 5353 and U.S. Pat. No. 5,001,233.

When any of R$_1$ to R$_{31}$ or Ar$_1$ to Ar$_6$ is or is a group substituted by alkyl, such alkyl groups are, for example, methyl, ethyl, isopropyl, n-butyl, tert-butyl, tert-amyl, 2-ethylhexyl, n-octyl, lauryl, n-tetradecyl, n-octadecyl or eicosyl; when said radicals are cycloalkyl, they are, for example, cyclopentyl, cyclohexyl, cyclooctyl or cyclododecyl; when said radicals are phenylalkyl, they are, for example, benzyl, phenethyl, α-methylbenzyl, α,α-dimethylbenzyl; when said radicals are aryl, they are, for example, phenyl, naphthyl, or when substituted by alkyl are, for example, tolyl and xylyl; when said radicals are alkyl interrupted by —O—, they are, for example, 3-oxaamyl and 3,6-dioxaoctyl; and when said radicals are alkenyl, they are, for example, allyl and oleyl.

Substrates in which the compounds of this invention are particularly useful are polyolefins such polypropylene and polyethylene.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylontrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acryl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability. 23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example, 2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example, 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |

| | |
|---|---|
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example, N,N'-di-(3,5-di-tert-butyl-4-hydroxyphenylpropionyl)-hexamethylenediamine
N,N'-di(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tertbutylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethyl-piperazinone), bis(1-octyloxy-2,2,6,6-tetramethylpiperidin-4-yl) sebacate.

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2- hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl,-stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhyroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxyamine derived from hydrogenated tallow amine.

8. Polyamide stabilizers, for example copper salts in combination with iodides and/or phosporus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2"-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N",N"'-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/$\beta,\beta,\beta',\beta'$-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/$\beta,\beta,\beta',\beta'$-tetramethyl-3,9-(2,4,8,10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine), N,N',N",N"'-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent bright-stocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: G$_1$-OCC-alkylene-COOG$_2$ wherein "alkylene" denotes an alkylene residue having from 2 to 14 carbon atoms and G$_1$ and G$_2$ are the same or different and each is an alkyl group having from 6 to 18 carbon atoms. Tri-esters which are of use as lubricating oil base stocks are those derived from trimethylolpropane and C$_6$–C$_{18}$ mono-carboxylic acids or mixtures thereof, whereas suitable tetra-esters include those derived from pentaerythritol and a C$_6$–C$_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol,2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol, 2,4,6-tricyclohexylphenol, 2,6-di-tert-butyl-4-methoxymethyl-phenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methyl-phenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol, 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methyl-phenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diamino-diphenyl-methane, N,N,N',N'-tetramethyl-4,4'-diamino-diphenylmethane, 1,2-di-(phenyl-amino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine, tert-octylated phenothiazine, 3,7-di-tert-octylphenothiazine.

Examples for other antioxidants

Aliphatic or aromatic phosphites, esters of thiodipropionic acid or of thiodiacetic acid, or salts of dithiocarbamic or dithiophosphoric acid.

Examples of metal passivators, for example for copper, are

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

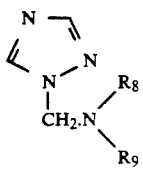

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g. I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula $$R_{12}-X_2-CH_2-CH(OH)-CH_2NR_{13}R_{14}$$

in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

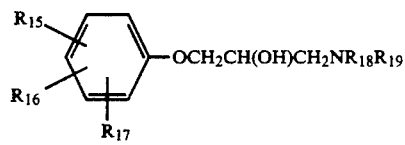

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are

Polymethacrylates, alkylated naphthalene derivatives.

Examples of dispersants/detergents are

Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are

Sulphur- and/or phosphorus- and/or halogen-containing compounds e.g. sulphurised vegetable oils, zinc dialkyldithiophosphates, tritolylphosphate, chlorinated paraffins, alkyl-and aryldi- and trisulphides, triphenyl-phosphorothionate.

EXAMPLE 1

2,6-Diphenyl-4-piperidone Ethylene Ketal

To a stirred suspension of 10.0 g (40 mmol) of 2,6-diphenyl-4-piperidone in 150 mL of ethylene glycol chilled to 0° C. is added 35 mL (275 mmol) of chlorotrimethylsilane over a one-hour period. The reaction mixture is warmed to room temperature and stirred for 15 hours. The reaction mixture is then quenched by carefully pouring it into 600 mL of saturated aqueous sodium bicarbonate solution. The product is extracted into ether (4×200 mL). The ether solution is dried over anhydrous sodium sulfate and the solvent is removed under reduced pressure. The residue is recrystallized from methanol to yield 8.1 g (69%) of the title compound as a white solid, melting at 125°-127° C.

Analysis: Calcd for $C_{19}H_{21}NO_2$: C, 77.3; H, 7.2; N, 4.7. Found: C, 76.7; H, 7.1; N, 4.5.

EXAMPLE 2

1-Hydroxy-2,6-diphenyl-4-piperidone Ethylene Ketal 812 mL (40.6 mmol) of dimethyldioxirane, 0.050M in acetone, is added via a cannula to a 0° C. solution of 12.0 g (40.6 mmol) of 2,6-diphenyl-4-piperidone ethylene petal in 100 mL acetone. After stirring for ten minutes at 0° C., the reaction mixture is concentrated under reduced pressure and the residue is recrystallized from methanol to yield 9.0 g (72%) of the title compound as a white solid, melting at 161°-162° C.

Analysis: Calcd for $C_{19}H_{21}NO_3$: C, 73.3; H, 6.8; N, 4.5. Found: C, 73.0; H, 6.8; N, 4.4.

EXAMPLE 3

2,6-Diphenyl-4-piperidone 1,2-Hexadecylene Ketal

A solution of 14.6 g (58.0 mmol) of 2,6-diphenyl-4-piperidone and 12.2 g (64 mmol) of p-toluenesulfonic acid monohydrate in 500 mL of toluene is refluxed and the azeotroping water is collected in a Dean Stark trap. When 1 mL of water is collected, 15.0 g (58.0 mmol) of 1,2-hexadecanediol (Aldrich) is added and the reaction is refluxed until another 1 mL of water is collected. The reaction mixture is cooled to room temperature and made basic with 50% aqueous sodium hydroxide solution. The organic layer is separated and the aqueous phase is extracted with toluene (2×100 mL). The combined organic phases are dried over anhydrous magnesium sulfate and the solvent is removed under reduced pressure. 11.0 g (38% yield) of the title compound is isolated after purification by liquid chromatography (LC) (silica gel, ethyl acetate/hexane) followed by recrystallization from ethanol: mp 63°-70° C.

Analysis: Calcd for $C_{33}H_{49}NO_2$: C, 80.6; H, 10.0; N, 2.8. Found: C, 80.4; H, 10.3; N, 2.6.

EXAMPLE 4

1-Hydroxy-2,6-diphenyl-4-piperidone 1,2-Hexadecylene Ketal

The general procedure of Example 2 is repeated using 10.9 g (22.2 mmol) of 2,6-diphenyl-4-piperidone 1,2-hexadecylene ketal and 376 mL (22.2 mmol) of dimethyldioxirane (0.059M in acetone). 7.3 g (65% yield) of the title compound is isolated as a white solid by recrystallization from ethanol: mp 98°-100° C.

Analysis: Calcd for $C_{33}H_{49}NO_3$: C, 78.1; H, 9.7; N, 2.8. Found: C, 78.4; H, 9.9; N, 2.7.

EXAMPLE 5

3,15-Diaza-7,11,18,21-tetraoxa-2,4,14,16-tetraphenyl-trispiro[5.2.2.5.2.2]henicosane A solution of 17.6 g (70.0 mmol) of 2,6-diphenyl-4-piperidone and 16.0 g (84 mmol) of p-toluenesulfonic acid monohydrate in 400 mL of toluene is refluxed and the azeotroping water is collected in a Dean Stark trap. When 1.5 mL of water is collected, 4.6 g (33.8 mmol) of pentaerythritol is added and the reaction is refluxed until another 1.2 mL of water is collected. The reaction mixture is cooled to room temperature and the solids are collected by filtration and washed with ethyl acetate. The solids are partitioned between ethyl acetate and 50% aqueous sodium hydroxide solution. The organic phase is dried over anhydrous magnesium sulfate and the solvent is removed under reduced pressure. Purification by LC (silica gel, ethyl acetate/hexanes) followed by recrystallization from hexanes/ethyl acetate yields 3.3 g (16% yield) of the title compound as a white solid melting at 122°-139° C.

EXAMPLE 6

3,15-Diaza-3,15-dihydroxy-7,11,18,21-tetraoxa-2,4,14,16-tetraphenyl-trispiro[5.2.2.5.2.2]henicosane The general procedure of Example 2 is repeated using 3.2 g (5.3 mmol) of the compound of Example 5 and 180 mL (10.6 mmol) of dimethyldioxirane (0.059M in acetone). 2.3 g (68% yield) of the title compound is isolated as a white solid after purification by LC (silica gel, ethyl acetate/hexanes): mp>260° C.

Analysis: Calcd for $C_{39}H_{42}N_2O_6$: C, 73.8; H, 6.7; N, 4.4. Found: C, 73.6; H, 6.7; N, 4.3.

EXAMPLE 7

3,15-Diaza-1,13-dimethyl-7,11,18,21-tetraoxa-2,4,14,16-tetraphenyl-trispiro[5.2.2.5.2.2]henicosane The general procedure of Example 5 is repeated using 20.5 g (80 mmol) of 2,6-diphenyl-3-methyl-4-piperidone, 16.7 g (88 mmol) of p-toluenesulfonic acid monohydrate and 5.4 g (40 mmol) of pentaerythritol. Purification by LC (silica gel, ethyl acetate/hexanes) yields 17.5 g (69%) of the title compound as a yellow foam melting at 183°-186° C.

Analysis: Calcd for $C_{41}H_{46}N_2O_4$:C, 78.1; H, 7.4; N, 4.4. Found: C, 78.5; H, 7.9; N, 4.2.

EXAMPLE 8

3,15-Diaza-3,15-dihydroxy-1,13-dimethyl-7,11,18,21-tetraoxa-2,4,14,16-tetraphenyl-trispiro[5.2.2.5.2.2-]henicosane The general procedure of Example 2 is repeated using 4.3 g (6.9 mmol) of the compound of Example 7 and 246 mL (13.8 mmol) of dimethyldioxirane (0.056M in acetone). 2.8 g (61% yield) of the title compound is isolated as a white solid by recrystallization from ethanol: mp 264°-267° C.

Analysis: Calcd for $C_{41}H_{46}N_2O_6$: C, 74.3; H, 7.0; N, 4.2. Found: C, 73.8; H, 6.7; N, 4.1.

EXAMPLE 9

9-Aza-3,3,7-trimethyl-1,5-dioxa-8,10-diphenylspiro[5,-5]undecane

The general procedure of Example 3 is followed using 10.0 g (38 mmol) of 3-methyl-2,6-diphenyl-4-piperidone, 4.6 g (44 mmol) of 2,2-dimethyl-1,3-propanediol and 8.4 g (44 mmol) of p-toluenesulfonic acid monohydrate. Recrystallization from hexane yields 7.6 g (57% yield) of the title compound as a white solid melting at 130°-131° C.

Analysis: Calcd for $C_{23}H_{29}NO_2$: C, 78.6; H, 8.3; N, 4.0. Found: C, 79.3; H, 8.4; N, 4.1.

EXAMPLE 10

9-Aza-9-hydroxy-3,3,7-trimethyl-1,5-dioxa-8,10-diphenylspiro[5,5]undecane

The general procedure of Example 2 is repeated using 4.0 g (11.4 mmol) of the compound of Example 9 and 203 mL (11.4 mmol) of dimethyldioxirane (0.056M in acetone). 2.5 g (60% yield) of the title compound is isolated as a white solid after recrystallization from ethanol: mp 175°-178° C.

Analysis: Calcd for $C_{23}H_{29}NO_3$: C, 75.2; H, 8.0; N, 3.8. Found: C, 75.0; H 8.2; N, 3.8.

EXAMPLE 11

1-Hydroxy-2,6-diphenyl-4,4-dimethoxypiperidine

To a solution of 6.0 g (21 mmol) 1-hydroxy-2,6-diphenyl-4-piperidone oxime (Diaz et al., Magn. Reson. Chem., 1989, 27, 823) and 5 ml(42 mmol) of 37% aqueous hydrochloric acid in 70 ml of methanol in a Parr bottle is added 0.5 g of 5% platinum on carbon catalyst. The mixture is shaken under 50 psi (3.5 Kg/cm$^2$) of hydrogen for three days. The reaction mixture is filtered and then concentrated. Purification by LC (silica gel, ethyl acetate/hexanes) yields 2.4 g (39.5%) of the title compound as a white solid melting at 172°–175° C.

Analysis: Calcd for $C_{19}H_{23}NO_3$: C, 72.8; H, 7.4; N, 4.5. Found: C, 72.9; H, 7.5, N, 4.4.

EXAMPLE 12

1-Hydroxy-2,6-diphenyl-4,4-dihexyloxypiperidine

A solution of 10.0 g (0.035 mole) 1-hydroxy-2,6-diphenyl-4-piperidone oxime, 22.0 g (0.22 moles) 1-hexanol and 7.0 g (0.073 moles) methanesulfonic acid in 250 mL tetrahydrofuran is heated at 60° C. for 12 hours. The solution is then washed three times with 10% aqueous sodium carbonate solution. The organic phase is dried over anhydrous sodium sulfate and concentrated. 3.2 g (20% yield) of the title compound is isolated as a clear oil after purification by LC (silica gel, ethyl acetate:hexane).

Analysis: Calcd for $C_{29}H_{43}NO_3$: C, 76.8; H, 9.6; N, 3.1. Found: C, 76.6; H, 9.8; N, 3.5.

EXAMPLE 13

1-Hydroxy-2,6-diphenyl-4,4-dioctyloxypiperidine

The general procedure of Example 12 is repeated using 10.0 g (0.035 mole) 1-hydroxy-2,6-diphenyl-4-piperidone oxime, 25.0 g (0.19 moles) 1-octanol and 7.0 g (0.073 moles) methanesulfonic acid. 5.8 g (32% yield) of the title compound is isolated as a clear oil after purification by LC (silica gel, ethyl acetate:hexane).

Analysis: Calcd for $C_{33}H_{51}NO_3$: C, 77.8; H, 10.1; N, 2.8. Found: C, 77.5; H, 10.3; N, 2.5.

EXAMPLE 14

Process Stabilization of Polypropylene at 525° F. (274° C.)

This example illustrates the process stabilizing effectiveness of the instant compounds in polypropylene.

The base formuation comprises unstabilized, old technology polypropylene (PROFAX 6501, Himont) containing 0.075% by weight of calcium stearate. The test additives are incorporated into the polypropylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion | |
|---|---|---|---|
|  |  | 1 | 5 |
| None | — | 10.5 | 61.7 |
| PS I | 0.075 | 5.0 | 21.5 |
| PS II | 0.075 | 3.1 | 4.5 |
| Compound of Example 2 | 0.075 | 3.8 | 6.6 |

*PS I is tris(2,4-di-tert-butylphenyl) phosphite.
PS II is 3,9-bis(2,4-di-tert-butylphenoxy)-2,4,8,10-tetraoxa-3,9-diphosphaspiro[5.5]undecane.

These results show that the 1-hydroxy-2,6-diaryl-4-piperidone ketals provide comparable melt flow stabilization to polypropylene as do the state of the art processing stabilizers.

EXAMPLE 15

Process Stabilization of Polypropylene at 525° F. (274° C.)

This example illustrates the process stabilizing effectiveness of the instant compounds in polypropylene in formulations also containing a phenolic antioxidant.

The results using the procedure described in Example 14 on polypropylene formulations containing an instant compound and a phenolic antioxidant are given in the table below.

| Additive* | Concentration (% by weight) | Melt Flow after extrusion | |
|---|---|---|---|
|  |  | 1 | 5 |
| AO A | 0.075 | 6.7 | 20.2 |
| AO A plus PS I | 0.075 0.075 | 3.6 | 7.0 |
| AO A plus PS II | 0.075 0.075 | 2.5 | 3.9 |
| AO A plus Example 2 Compound | 0.075 0.075 | 3.3 | 5.8 |

*AO A is neopentanetetrayl tetrakis(3,5-di-tert-butyl-4-hydroxyhydrocinnamate).
PS I is tris(2,4-di-tert-butylphenyl)phosphite.
PS II is 3,9-bis(2,4-di-tert-butylphenoxy)-2,4,8,10-tetraoxa-3,9-diphosphaspiro[5.5]undecane.

These results show that the 1-hydroxy-2,6-diaryl-4-piperidone ketals in combination with a phenolic antioxidant provide comparable melt flow stabilization to polypropylene as do the state of the art processing stabilizers.

EXAMPLE 16

Process Stabilization of Polypropylene at 525° F. (274° C.)

This example illustrates the process stabilizing effectiveness of the instant compounds in polypropylene formulations also containing a phenolic antioxidant.

The base formulation comprises unstabilized, new technology polypropylene (PROFAX 6301, Himont) containing 0.075% by weight of calcium stearate. The test additives are incorporated into the polypropylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion 1 | 5 |
|---|---|---|---|
| AO A | 0.075 | 21.1 | 35.4 |
| AO A plus | 0.075 | | |
| PS I | 0.075 | 15.6 | 21.1 |
| AO A plus | 0.075 | | |
| PS II | 0.075 | 13.1 | 16.3 |
| AO A plus | 0.075 | | |
| Example 4 Compound | 0.075 | 16.5 | 23.1 |
| AO A plus | 0.075 | | |
| Example 8 Compound | 0.075 | 16.2 | 22.4 |
| AO A plus | 0.075 | | |
| Example 10 Compound | 0.075 | 15.8 | 22.7 |

*AO A is neopentanetetrayl tetrakis(3,5-di-tert-butyl-4-hydroxyhydrocinnamate).
PS I is tris(2,4-di-tert-butylphenyl)phosphite.
PS II is 3,9-bis(2,4-di-tert-butylphenoxy)-2,4,8,10-tetraoxa-3,9-diphosphaspiro[5.5]undecane.

These results show that the 1-hydroxy-2,6-diaryl-4-piperidone ketals in combination with a phenolic antioxidant provide comparable melt flow stabilization to polypropylene as do the state of the art processing stabilizers.

EXAMPLE 17

Color Stabilization of Polypropylene

This example illustrates the color stabilizing effectiveness of the instant compounds in combination with a phenolic antioxidant in polypropylene.

Using the procedure described in Example 15, polypropylene containing a phenolic antioxidant in combination with an instant compound is extruded into pellets. Using the pellets obtained after each of the first and fifth extrusions as described in Example 11. The pellets are compression molded into 125 mil (3.2 mm) thick plaques at 193° C. Specimen yellowness index (YI) values are determinated according to ASTM method D1925. Lower YI values indicates less discoloration. The results are given in the table below.

| Additive* | Concentration (% by weight) | Yellowness YI after Extrusion 1 | 5 |
|---|---|---|---|
| AO A | 0.075 | 8.05 | 8.60 |
| AO A plus | 0.075 | | |
| PS I | 0.075 | 8.35 | 9.72 |
| AO A plus | 0.075 | | |
| PS II | 0.075 | 7.39 | 9.72 |
| AO A plus | 0.075 | | |
| Example 2 Compound | 0.075 | 6.21 | 7.05 |

*AO A is neopentanetetrayl tetrakis(3,5-di-tert-butyl-4-hydroxyhydrocinnamate).
PS I is tris(2,4-di-tert-butylphenyl) phosphite.

PS II is 3,9-bis(2,4-di-tert-butylphenoxy)-2,4,8,10-tetraoxa-3,9-diphosphaspiro[5.5]undecane.

These results show that the 1-hydroxy-2,6-diaryl-4-piperidone ketals in combination with a phenolic antioxidant provide superior resistance to discolaration during the processing of polypropylene than do the state of the art processing stabilizers.

EXAMPLE 18

This example illustrates the color stabilizing effectiveness of the instant compounds in combination with a phenolic antioxidant in polypropylene.

Using the procedure described in Example 16, polypropylene containing a phenolic antioxidant in combination with an instant compound is extruded into pellets. Using the pellets obtained after each of the first and fifth extrusions as described in Example 16. The pellets are compression molded into 125 mil (3.2 mm) thick plaques at 193° C. Specimen yellowness index (YI) values are determined according to ASTM method D1925. Lower YI values indicates less discoloration. The results are given in the table below.

| Additive* | Concentration (% by weight) | Yellowness YI after Extrusion 1 | 5 |
|---|---|---|---|
| AO A | 0.075 | 9.36 | 11.93 |
| AO A plus | 0.075 | | |
| PS I | 0.075 | 12.03 | 15.44 |
| AO A plus | 0.075 | | |
| PS II | 0.075 | 5.19 | 8.86 |
| AO A plus | 0.075 | | |
| Example 4 Compound | 0.075 | 4.89 | 5.92 |
| AO A plus | 0.075 | | |
| Example 8 Compound | 0.075 | 5.03 | 6.27 |
| AO A plus | 0.075 | | |
| Example 10 Compound | 0.075 | 4.85 | 6.00 |

*AO A is neopentanetetrayl tetrakis(3,5-di-tert-butyl-4-hydroxyhydrocinnamate).
PS I is tris(2,4-di-tert-butylphenyl)phosphite.
PS II is 3,9-bis(2,4-di-tert-butylphenoxy)-2,4,8,10-tetraoxa-3,9-diphosphaspiro[5.5]undecane.

These results show that the 1-hydroxy-2,6-diaryl-4-piperidone ketals in combination with a phenolic antioxidant provide superior resistance to discoloration during the processing of polypropylene than do the state of the art processing stabilizers.

EXAMPLE 19

Long Term Heat Aging Stability of Polypropylene

Extruded pellets (of Example 16), after the first pass, are compression molded into 125 mil (3.2 mm) plaques at 450° F. (232° C.) and then oven aged at 150° C. in a forced draft oven equipped with a rotating carousel. The time, in days, to reach a yellowness index (YI) color of 50 units is deemed to represent failure. The results are given in the table below.

| Additive* | Concentration (% by weight) | Days to Failure |
|---|---|---|
| AO A | 0.075 | 26 |
| AO A plus | 0.075 | |
| PS I | 0.075 | 27 |
| AO A plus | 0.075 | |
| PS II | 0.075 | 38 |
| AO A plus | 0.075 | |
| Example 4 Compound | 0.075 | 36 |
| AO A plus | 0.075 | |
| Example 8 Compound | 0.075 | 34 |
| AO A plus | 0.075 | |
| Example 10 | 0.075 | 31 |

-continued

| Additive* | Concentration (% by weight) | Days to Failure |
|---|---|---|
| Compound | | |

*AO A is neopentanetetrayl tetrakis(3,5-di-tert-butyl-4-hydroxyhydrocinnamate).
PS I is tris(2,4-di-tert-butylphenyl)phosphite.
PS II is 3,9-bis(2,4-di-tert-butylphenoxy)-2,4,8,10-tetraoxa-3,9-diphosphaspiro[5.5]undecane.

These results show that the 1-hydroxy-2,6-diaryl-4-piperidone ketals in combination with a phenolic antioxidant provide comparable long term heat aging stability to the state of the art processing stabilizers.

EXAMPLE 20

Long Term Heat Aging Stability of Polypropylene

Extruded pellets (of Example 16), after the first pass, are compression molded into 40 mil (1 mm) plaques at 450° F. (232° C.) and then oven aged at 150° C. in a forced draft oven equipped with a rotating carousel. The time, in days, to physical failure is determined by a 90° bend test. The results are given in the table below.

| Additive* | Concentration (% by weight) | Days to Failure |
|---|---|---|
| AO A | 0.075 | 21 |
| AO A plus | 0.075 | |
| PS I | 0.075 | 22 |
| AO A plus | 0.075 | |
| PS II | 0.075 | 36 |
| AO A plus | 0.075 | |
| Example 4 Compound | 0.075 | 26 |
| AO A plus | 0.075 | |
| Example 8 Compound | 0.075 | 36 |
| AO A plus | 0.075 | |
| Example 10 Compound | 0.075 | 26 |

*AO A is neopentanetetrayl tetrakis(3,5-di-tert-butyl-4-hydroxyhydrocinnamate).
PS I is tris(2,4-di-tert-butylphenyl)phosphite.
PS II is 3,9-bis(2,4-di-tert-butylphenoxy)-2,4,8,10-tetraoxa-3,9-diphosph aspiro[5.5]undecane.

These results show that the 1-hydroxy-2,6-diaryl-4-piperidone ketals in combination with a phenolic antioxidant provide comparable long term heat aging stability of the state of the art processing stabilizers.

What is claimed is:

1. A compound of formula I, II or III

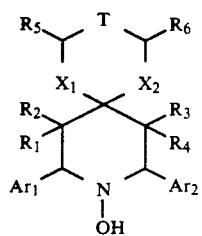

I

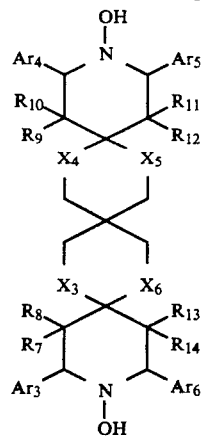

II

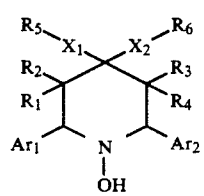

III wherein
$Ar_1$, $Ar_2$, $Ar_3$, $Ar_4$, $Ar_5$ and $Ar_6$ are independently aryl of 6 to 10 carbon atoms or said aryl substituted by one to three substituents selected from the group consisting of alkyl of 1 to 20 carbon atoms, cycloalkyl of 5 to 12 carbon atoms, phenylalkyl of 7 to 15 carbon atoms, —$COOR_{15}$ where $R_{15}$ is hydrogen or alkyl of 1 to 20 carbon atoms, —$COR_{16}$ where $R_{16}$ is alkyl of 1 to 20 carbon atoms, —$NR_{17}R_{18}$ where $R_{17}$ and $R_{18}$ are independently hydrogen or alkyl of 1 to 20 carbon atoms, —$SR_{19}$ where $R_{19}$ is aryl of 6 to 10 carbon atoms or alkyl of 1 to 20 carbon atoms, —OH, —$OCH_3$, —CN, —$CF_3$, —$NO_2$, —F, —Cl, —Br and —I;

$R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently hydrogen, a linear or branched alkyl of 1 to 30 carbon atoms, said alkyl terminated with —$OR_{20}$, —$NR_{21}R_{22}$, —$SR_{23}$, —$COOR_{24}$ or —$CONR_{25}R_{26}$, where $R_{20}$, $R_{21}$, $R_{22}$, $R_{23}$, $R_{24}$, $R_{25}$ and $R_{26}$ are independently hydrogen, alkyl of 1 to 20 carbon atoms or alkenyl of 3 to 18 carbon atoms, said alkyl interrupted by one or more —O—, —S—, —SO—, —$SO_2$—, —CO—, —COO—, —OCO—, —$CONR_{27}$—, —$NR_{27}CO$— or —$NR_{28}$— where $R_{27}$ and $R_{28}$ independently have the same meaning as $R_{20}$, alkenyl of 3 to 20 carbon atoms, aryl of 6 to 10 carbon atoms, said aryl substituted by one to three substituents selected from the group consisting of alkyl of 1 to 20 carbon atoms, cycloalkyl of 5 to 12 carbon atoms, phenylalkyl of 7 to 15 carbon atoms, —$COOR_{29}$ where $R_{29}$ is hydrogen or alkyl of 1 to 20 carbon atoms, —$COR_{30}$ where $R_{30}$ is alkyl of 1 to 20 carbon atoms, —$NR_{31}R_{32}$ where $R_{31}$ and $R_{32}$ are independently hydrogen or alkyl of 1 to 20 carbon atoms, —$SR_{33}$ where $R_{33}$ is aryl of 6 to 10 carbon atoms or alkyl of 1 to 20 carbon atoms, —OH, —$OCH_3$, —CN, —$CF_3$, —$NO_2$, —F, —Cl, —Br and —I;

T is a direct bond or —CR$_{34}$R$_{35}$— where R$_{34}$ and R$_{35}$ independently have the same meaning as R$_1$; and X$_1$, X$_2$, X$_3$, X$_4$, X$_5$ and X$_6$ are independently —O—, —S— or —NR$_{36}$— where R$_{36}$ has the same meaning as R$_{20}$.

2. A compound according to claim 1 wherein Ar$_1$, Ar$_2$, Ar$_3$, Ar$_4$, Ar$_5$ or Ar$_6$ is phenyl.

3. A compound according to claim 1 wherein R$_1$, R$_2$, R$_3$, R$_4$, R$_7$, R$_8$, R$_9$, R$_{10}$, R$_{11}$, R$_{12}$, R$_{13}$ and R$_{14}$ are independently hydrogen or methyl.

4. A compound according to claim 1 where in formula I, R$_5$ and R$_6$ are hydrogen and T is a direct bond; or R$_5$ is hydrogen and R$_6$ is tetradecyl, and T is a direct bond; or R$_5$ and R$_6$ are hydrogen and T is —C(CH$_3$)$_2$—.

5. A compound according to claim 1 where in formula III, R$_5$ and R$_6$ are alkyl of 6 to 12 carbon atoms.

6. A compound according to claim 1 wherein X$_1$, X$_2$, X$_3$, X$_4$, X$_5$ or X$_6$ is —O—.

7. The compound according to claim 1 which is 1-hydroxy-2,6-diphenyl-4-piperidone ethylene ketal; 1-hydroxy-2,6-diphenyl-4-piperidone 1,2-hexadecylene ketal; 3,15-diaza-3,15-dihydroxy-7,11,18,21-tetraoxa-2,4,14,16-tetraphenyl-trispiro[5.2.2.5.2.2]henicosane; 3,15-diaza-3,15-dihydroxy-1,13-dimethyl-7,11,18,21-tetraoxa-2,4,14,16-tetraphenyl-trispiro[5.2.2.5.2.2]henicosane; 9-aza-9-hydroxy-3,3,7-trimethyl-1,5-dioxa-8,10-diphenylspiro[5,5]undecane; 1-hydroxy-2,6-diphenyl-4,4-dimethoxypiperidine; 1-hydroxy-2,6-diphenyl-4,4-dihexyloxypiperidine; or 1-hydroxy-2,6-diphenyl-4,4-dioctyloxypiperidine.

8. A stabilized composition which comprises
   (a) an organic polymer subject to thermal and oxidative degradation; and
   (b) an effective stabilizing amount of a compound of formula I, II or III

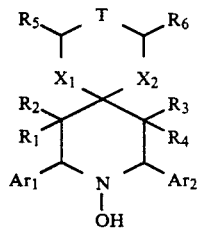  I

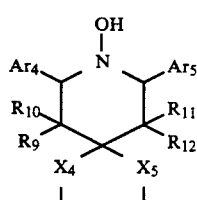  II

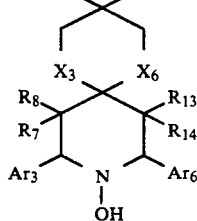

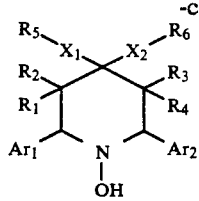  III wherein
Ar$_1$, Ar$_2$, Ar$_3$, Ar$_4$, Ar$_5$ and Ar$_6$ are independently aryl of 6 to 10 carbon atoms or said aryl substituted by one to three substituents selected from the group consisting of alkyl of 1 to 20 carbon atoms, cycloalkyl of 5 to 12 carbon atoms, phenylalkyl of 7 to 15 carbon atoms, —COOR$_{15}$ where R$_{15}$ is hydrogen or alkyl of 1 to 20 carbon atoms, —COR$_{16}$ where R$_{16}$ is alkyl of 1 to 20 carbon atoms, —NR$_{17}$R$_{18}$ where R$_{17}$ and R$_{18}$ are independently hydrogen or alkyl of 1 to 20 carbon atoms, —SR$_{19}$ where R$_{19}$ is aryl of 6 to 10 carbon atoms or alkyl of 1 to 20 carbon atoms, —OH, —OCH$_3$, —CN, —CF$_3$, —NO$_2$, —F, —Cl, —Br and —I;

R$_1$, R$_2$, R$_3$, R$_4$, R$_5$, R$_6$, R$_7$, R$_8$, R$_9$, R$_{10}$, R$_{11}$, R$_{12}$, R$_{13}$ and R$_{14}$ are independently hydrogen, a linear or branched alkyl of 1 to 30 carbon atoms, said alkyl terminated with —OR$_{20}$, —NR$_{21}$R$_{22}$, —SR$_{23}$, —COOR$_{24}$ or —CONR$_{25}$R$_{26}$, where R$_{20}$, R$_{21}$, R$_{22}$, R$_{23}$, R$_{24}$, R$_{25}$ and R$_{26}$ are independently hydrogen, alkyl of 1 to 20 carbon atoms or alkenyl of 3 to 18 carbon atoms, said alkyl interrupted by one or more —O—, —S—, —SO—, —SO$_2$—, —CO—, —COO—, —OCO—, —CONR$_{27}$—, —NR$_{27}$CO— or —NR$_{28}$— where R$_{27}$ and R$_{28}$ independently have the same meaning as R$_{20}$, alkenyl of 3 to 20 carbon atoms, aryl of 6 to 10 carbon atoms, said aryl substituted by one to three substituents selected from the group consisting of alkyl of 1 to 20 carbon atoms, cycloalkyl of 5 to 12 carbon atoms, phenylalkyl of 7 to 15 carbon atoms, —COOR$_{29}$ where R$_{29}$ is hydrogen or alkyl of 1 to 20 carbon atoms, —COR$_{30}$ where R$_{30}$ is alkyl of 1 to 20 carbon atoms, —NR$_{31}$R$_{32}$ where R$_{31}$ and R$_{32}$ are independently hydrogen or alkyl of 1 to 20 carbon atoms, —SR$_{33}$ where R$_{33}$ is aryl of 6 to 10 carbon atoms or alkyl of 1 to 20 carbon atoms, —OH, —OCH$_3$, —CN, —CF$_3$, —NO$_2$, —F, —Cl, —Br and —I;

T is a direct bond or —CR$_{34}$R$_{35}$— where R$_{34}$ and R$_{35}$ independently have the same meaning as R$_1$; and X$_1$, X$_2$, X$_3$, X$_4$, X$_5$ and X$_6$ are independently —O—, —S— or —NR$_{36}$— where R$_{36}$ has the same meaning as R$_{20}$.

9. A composition according to claim 8 wherein the organic polymer is a polyolefin.

10. A composition according to claim 9 wherein the polyolefin is polypropylene.

11. A composition according to claim 8 where in the compound of component (b) of formula I, II or III, Ar$_1$, Ar$_2$, Ar$_3$, Ar$_4$, Ar$_5$ or Ar$_6$ is phenyl.

12. A composition according to claim 8 where in the compound of component (b) of formula I, II or III, R$_1$, R$_2$, R$_3$, R$_4$, R$_7$, R$_8$, R$_9$, R$_{10}$, R$_{11}$, R$_{12}$, R$_{13}$ and R$_{14}$ are independently hydrogen or methyl.

13. A composition according to claim 8 where in the compound of component (b) of formula I, R$_5$ and R$_6$ are hydrogen and T is a direct bond; or R$_5$ is hydrogen and R$_6$ is tetradecyl, and T is a direct bond; or R$_5$ and R$_6$ are hydrogen and T is —C(CH$_3$)$_2$—.

14. A composition according to claim 8 where in the compound of component (b) of formula III, R$_5$ and R$_6$ are alkyl of 6 to 12 carbon atoms.

15. A composition according to claim 8 where in the compound of component (b) of formula I, II or III, X$_1$, X$_2$, X$_3$, X$_4$, X$_5$ or X$_6$ is —O—.

16. A composition according to claim 8 wherein the compound of component (b) is 1-hydroxy-2,6-diphenyl-4-piperidone ethylene ketal; 1-hydroxy-2,6-diphenyl-4-piperidone 1,2-hexadecylene ketal; 3,15-diaza-3,15-dihydroxy-7,11,18,21-tetraoxa-2,4,14,16-tetraphenyl-trispiro[5.2.2.5.2.2]henicosane; 3,15-diaza-3,15-dihydroxy-1,13-dimethyl-7,11,18,21-tetraoxa-2,4,14,16-tetraphenyl-trispiro[5.2.2.5.2.2.]henicosane; 9-aza-9-hydroxy-3,3,7-trimethyl-1,5-dioxa-8,10-diphenyl-spiro[5,5]undecane; 1-hydroxy-2,6-diphenyl-4,4-dimethoxypiperidine; 1-hydroxy-2,6-diphenyl-4,4-dihexyloxypiperidine; or 1-hydroxy-2,6-diphenyl-4,4-dioctyloxypiperidine.

17. A composition according to claim 8 which additionally contains an effective stabilizing amount of a phenolic antioxidant selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butyl-phenol), 1,3,5-tris(2,6-dimethyl-4-tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

18. A composition according to claim 17 wherein the phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)-benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

19. A compound of the formula IV, V or VI

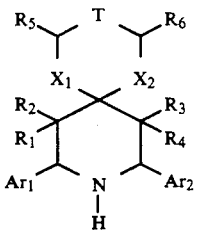

IV

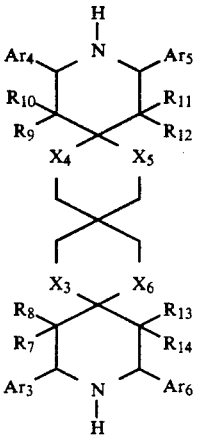

V

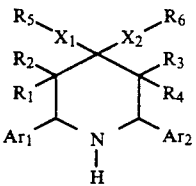

VI wherein
Ar$_1$, Ar$_2$, Ar$_3$, Ar$_4$, Ar$_5$ and Ar$_6$ are independently aryl of 6 to 10 carbon atoms or said aryl substituted by one to three substituents selected from the group consisting of alkyl of 1 to 20 carbon atoms, cycloalkyl of 5 to 12 carbon atoms, phenylalkyl of 7 to 15 carbon atoms, —COOR$_{15}$ where R$_{15}$ is hydrogen or alkyl of 1 to 20 carbon atoms, —COR$_{16}$ where R$_{16}$ is alkyl of 1 to 20 carbon atoms, —NR$_{17}$R$_{18}$ where R$_{17}$ and R$_{18}$ are independently hydrogen or alkyl of 1 to 20 carbon atoms, —SR$_{19}$ where R$_{19}$ is aryl of 6 to 10 carbon atoms or alkyl of 1 to 20 carbon atoms —OH, —OCH$_3$, —CN, —CF$_3$, —NO$_2$, —F, —Cl, —Br and —I;
R$_1$, R$_2$, R$_3$, R$_4$, R$_5$, R$_6$, R$_7$, R$_8$, R$_9$, R$_{10}$, R$_{11}$, R$_{12}$, R$_{13}$ and R$_{14}$ are independently hydrogens, a linear or branched alkyl of 1 to 30 carbon atoms said alkyl terminated with —OR$_{20}$, —NR$_{21}$R$_{22}$, —SR$_{23}$, —COOR$_{24}$ or —CONR$_{25}$R$_{26}$, where R$_{20}$, R$_{21}$, R$_{22}$, R$_{23}$, R$_{24}$, R$_{25}$ and R$_{26}$ are independently hydrogen, alkyl of 1 to 20 carbon atoms or alkenyl of 3 to 18 carbon atoms said alkyl interrupted by one or more —O—, —S—, —SO—, —SO$_2$—, —CO—, —COO—, —OCO—, —CONR$_{27}$—, —NR$_{27}$CO— or —NR$_{28}$— where R$_{27}$ and R$_{28}$ independently have the same meaning as R$_{20}$ alkenyl of 3 to 20 carbon atoms aryl of 6 to 10 carbon atoms said aryl substituted by one to three substituents selected from the group consisting of alkyl of 1 to 20 carbon atoms, cycloalkyl of 5 to 12 carbon atoms, phenylalkyl of 7 to 15 carbon atoms, —COOR$_{29}$ where $R_{29}$ is hydrogen or alkyl of 1 to 20 carbon atoms, —$COR_{30}$ where $R_{30}$ is alkyl of 1 to 20 carbon atoms, —$NR_{31}R_{32}$ where $R_{31}$ and $R_{32}$ are independently hydrogen or alkyl of 1 to 20 carbon atoms, —$SR_{33}$ where $R_{33}$ is aryl of 6 to 10 carbon atoms or alkyl of 1 to 20 carbon atoms, —OH, —$OCH_3$, —CN, —$CF_3$, —$NO_2$, —F, —Cl, —Br and —I;

T is a direct bond or —$CR_{34}R_{35}$— where $R_{34}$ and $R_{35}$ independently have the same meaning as $R_1$; and $X_1$, $X_2$, $X_3$, $X_4$, $X_5$ and $X_6$ are independently —O—, —S— or —$NR_{36}$— where $R_{36}$ has the same meaning as $R_{20}$.

20. The compound according to claim 19 which is 2,6-diphenyl-4-piperidone ethylene ketal; 2,6-diphenyl-4-piperidone 1,2-hexadecylene ketal; 3,15-diaza-7,11,18,21-tetraoxa-2,4,14,16-tetraphenyl-trispiro[5.2.2.5.2.2]henicosane; 3,15-diaza-1,13-dimethyl-7,11,18,21-tetraoxa-2,4,14,16-tetraphenyl-trispiro[5.2.2.5.2.2.]henicosane; or 9-aza-3,3,7-trimethyl-1,5-dioxa-8,10-diphenylspiro[5,5]undecane.

* * * * *